United States Patent [19]
Gieselmann

[11] Patent Number: 5,879,662
[45] Date of Patent: Mar. 9, 1999

[54] ORAL ECHO CONTRAST MEDIUM FOR ULTRASONIC DIAGNOSIS

[76] Inventor: Thomas Gieselmann, Danziger Strasse 6, D-56288 Kastellaun, Germany

[21] Appl. No.: 765,499

[22] PCT Filed: Jul. 3, 1995

[86] PCT No.: PCT/EP95/02569

§ 371 Date: Jun. 13, 1997

§ 102(e) Date: Jun. 13, 1997

[87] PCT Pub. No.: WO96/01654

PCT Pub. Date: Jan. 25, 1996

[30] Foreign Application Priority Data

Jul. 9, 1994 [DE] Germany .......................... 44 24 233.6

[51] Int. Cl.⁶ ........................... A61K 49/04; A61K 47/30
[52] U.S. Cl. ......................................... 424/9.5; 514/772.3
[58] Field of Search ........................... 424/9.5, 9.1, 9.52, 424/70.15; 514/772.3, 772.2

[56] References Cited

U.S. PATENT DOCUMENTS 5,370,901  12/1994  Tournier et al. ...................... 427/2.12
5,420,176   5/1995  Unger et al. ........................... 523/205

OTHER PUBLICATIONS

Takayama et al. "Dissolution Behavior of Flufenamic Acid Dispersed in Crosslinked Insoluble Polyvinylpyrrolidone," Chem. Pharm. Bull., vol. 30, No. 10, pp. 3701–3710, 1982.

*Primary Examiner*—José G. Dees
*Assistant Examiner*—Michael G. Hartley
*Attorney, Agent, or Firm*—Antonelli, Terry, Stout & Kraus, LLP

[57] ABSTRACT

An oral contrast agent for use in ultrasound diagnostic procedures in human medicine to create an image of the gastrointestinal tract. The oral contrast agent contains at least one thickening agent and an insoluble polyvinylpolypyrrolidone.

10 Claims, No Drawings

ORAL ECHO CONTRAST MEDIUM FOR ULTRASONIC DIAGNOSIS

The invention relates to an oral echo contrast medium for ultrasonic diagnosis for displaying the entire gastrointestinal tract. An echo contrast medium must meet the following requirements:

It must not be toxic, it must not influence the intestinal peristalsis, it must not be resorbed, and it must not cause any sonic shadows that would make diagnosis more difficult. In addition, the echo contrast medium must dilate the intestine and fill the intestine homogeneously.

In the past, water, fruit juices, and milk have been used primarily as aids in oral echo contrast media for ultrasonic diagnosis. The results of ultrasonic examinations performed with them are unsatisfactory, however. In addition, patients must drink between one and two liters of fluid.

Recently, attempts have also been made to use cellulose fibers or other hollow bodies containing air, or laminated silicates as echo contrast media, but they have proven to be disadvantageous because sonic shadows occur which make a diagnosis impossible, especially in deeper layers.

The goal of the invention is to propose an oral echo contrast medium for ultrasonic diagnosis in human medicine to investigate the gastrointestinal tract, said medium permitting a detailed representation of the investigated area and suppressing the development of interfering sonic shadows.

Surprisingly, it has been found that an oral contrast medium containing the following components in a liter of water:

A) 0.5 to 80 g, preferably 1 to 40 g of at least one thickening agent;

B) 4 to 100 g, preferably 10 to 60 g of cross-linked insoluble polyvinylpolypyrrolidone (PVPP);

C) 0 to 40 g, preferably 8 to 20 g of mannite;

D) 0 to 2 g, preferably 0.5 to 1.5 g of aromatic substances;

E) 0 to 50 g, preferably 10 to 30 g of a solvent for one of components A;

F) 0 to 5 g, preferably 0.1 to 3 g of non-ionic surfactant, meets these requirements. In particular, it is the combination of at least one thickening agent and a cross-linked insoluble polyvinylpolypyrrolidone, also referred to as, that produces an increase in contrast that leads to the desired successful diagnosis.

In particular, a sharp demarcation of the intestinal mucosa is obtained with the oral echo contrast medium according to the invention, thus providing a very good opportunity of investigating other organs through the sonic window produced in this manner.

All of the components used in the oral echo contrast medium according to the invention must be investigated to ensure that they are not toxic, do not influence intestinal peristalsis, are not resorbed, and do not produce any sonic shadows but dilate the intestine and fill it homogeneously.

In particular organic natural thickening agents and/or organically converted natural substances and/or completely synthetic organic substances are particularly useful as thickening agents.

Preferred organic natural thickening agents include agar-agar, gum tragacanth, carrageenan, alginates, gum arabic, pectins, polyoses, guar powder, starch, xanthene, dextrins, gelatins, and/or casein. Thickening agents based on organically converted natural substances include in particular carboxymethylcellulose and/or cellulose ether.

Organic natural thickening agents and thickening agents based on organically converted natural substances are overwhelmingly readily soluble in water.

Fully synthetic organic thickening agents can also include medium and high molecular weight polyvinylpyrrolidones, also known as povidones, that are very readily soluble in water.

In order to be able to wet the intestinal mucosa better, it is proposed according to the invention to add to the echo contrast medium a suitable pharmaceutically approved surfactant or one approved by legislation governing food, preferably a non-ionic surfactant. A poloxamer that acts as a non-ionic surfactant can be used, for example. It is also possible to use so-called sugar surfactants. Other surfactants approved by legislation governing food can also be used for the desired purpose.

In addition, mannite can be added to the echo contrast medium according to the invention since this substance, in addition to having a sweetening effect, also has a mildly laxative action. In addition, the poloxamer, when added as a surfactant for wetting the intestinal mucosa better, has a mildly laxative action.

Such a laxative effect however is likewise desirable for the comfort of the patients treated with the echo contrast medium according to the invention.

In addition, taste corrigents, especially aromatic substances and possibly also a preservative, can be added to the echo contrast medium according to the invention. Aromatic substances and preservatives approved under legislation governing food can also be employed for this purpose.

The preferred amounts of the individual components are listed in claim 1 with the amounts calculated on the basis of one liter of water, so that a pasty echo contrast medium that can be readily ingested by the patient is obtained.

In order to achieve a uniform distribution of the individual components in the echo contrast medium, it may be advantageous to distribute one of the thickening agents separately in a solvent and then add it to the water in this previous dilution. Such an additional solvent includes small amounts of propylene glycol. In addition, other suitable solvents that have been approved by legislation governing food can be employed.

A preferred composition of an echo contrast medium according to the invention and showing the amounts of the components in one liter of water is the following:

A) 2 to 10 g xanthene and 2 to 3 g povidone,

B) 20 to 60 g PVPP,

C) 5 to 30 g mannite,

D) 0.1 to 1.2 g aromatic substances, as taste corrigents

E) 10 to 30 g propylene glycol, and

F) 0 to 5 g poloxamer.

Tests on human beings using an echo contrast medium prepared according to the invention have demonstrated a good tolerance and surprising echogenic properties. Oral echo contrast media according to the invention produce uniform sound absorption or sound reflection during ultrasonic diagnosis, with simultaneous expulsion of interfering air. A detailed representation of the entire gastrointestinal tract is obtained. In addition, the wall thickness of the stomach and intestine can be shown readily.

The invention will now be described with reference to two sample compositions for an oral echo contrast medium.

EXAMPLE 1

| | |
|---|---|
| Component A: | Xanthene gum (trade name: Keltrol F ® made by Kelco) 4 g |
| | Povidone (trade name: Kollidon 16 from BASF) 20 g |
| Component B: | PVPP (trade name: Polyplasidone XL ® from GAF) 36 g |
| Component C: | Mannite, 10 g |
| Component D: | Aromatic substance, 1.0 g |
| Component E: | Propylene glycol, 20 g |
| Water: | 1 liter (1000 g) |

To prepare the echo contrast medium, the mannite, povidone, and aromatic substance were dissolved in water. Then the PVPP was suspended.

In a separate vessel, the xanthene was distributed homogeneously in propylene glycol and added to the above aqueous liquid while stirring.

After the xanthene has swelled, the preparation is ready to use as an echo contrast medium.

EXAMPLE 2

| Component A: | Xanthene, same as Example 1, 3.0 g |
| | Povidone, same as Example 1, 3.0 g |
| Component B: | PVPP, same as Example 1, 40.0 g |
| Component C: | Mannite, 15.0 g |
| Component D: | Aromatic substance, 1.0 g |
| Component E: | Propylene glycol, 20.0 g |
| Component F: | Poloxamer 188, 2.0 g |
| Water: | 1 liter |

Preparation is as in Example 1. Component F is dissolved in water together with mannite, povidone, and an aromatic substance.

I claim:

1. Echo contrast medium containing the following components in one liter of water:
   A) 1 to 40 g of at least one thickening agent;
   B) 10 to 60 g of cross-linked insoluble polyvinylpolypyrrolidone (PVPP);
   C) 8 to 20 g of mannite;
   D) 0.5 to 1.5 g of a taste corrigent;
   E) 10 to 30 g of a solvent for at least one thickening agent;
   F) 0 to 5 g of non-ionic surfactant.

2. Echo contrast medium according to the claim 1, characterized in that organic natural thickening agents and/or organically converted natural substances and/or fully synthetic organic substances are used as thickening agents.

3. Echo contrast medium according to claim 1, characterized in that agar-agar, gum tragacanth, carrageenan, alginates, gum arabic, pectins, polyoses, guar powder, starch, xanthene, dextrins, gelatins, and/or casein are used as organic natural thickening agents.

4. Echo contrast medium according to claim 1, characterized in that carboxymethylcellulose and/or cellulose ether are used as thickening agents based on organically converted natural materials.

5. Echo contrast medium according to one claim 1, characterized in that medium or high molecular weight povidones (polyvinylpyrrolidones) are used as fully synthetic thickening agents.

6. Echo contrast medium according to claim 1, characterized in that at least one of the thickening agents used is readily soluble in water.

7. Echo contrast medium according to one of claim 1, characterized in that a poloxamer that has been approved by legislation governing food and is a non-ionic surfactant is used as component F.

8. Echo contrast medium according to claim 1, characterized in that propylene glycol is used as the solvent.

9. Echo contrast medium characterized by a composition that contains the following amounts of components in one liter of water:
   A) 2 to 10 g xanthene and 2 to 3 g povidone,
   B) 20 to 60 g PVPP,
   C) 5 to 30 g mannite,
   D) 0.1 to 1.2 g aromatic substance as a taste corrigent,
   E) 10 to 30 g propylene glycol, and
   F) 0 to 5 g poloxamer.

10. Echo contrast medium according to claim 1, consisting essentially of the following components in one liter of water:
   A) 1 to 40 g of at least one thickening agent;
   B) 10 to 60 g of cross-linked insoluble polyvinylpolypyrrolidone (PVPP);
   C) 8 to 20 g of mannite;
   D) 0.5 to 1.5 g of a taste corrigent;
   E) 10 to 30 g of a solvent for at least one thickening agent;
   F) 0.1 to 3 g of non-ionic surfactant.

* * * * *